United States Patent [19]
Shim et al.

[11] 3,959,414
[45] May 25, 1976

[54] METHOD OF PREPARING STABLE CONDENSATION PRODUCTS USING A WATER-ALKYLENE OXIDE TREATMENT AND PRODUCTS THEREFROM

[75] Inventors: Kyung S. Shim, Irvington; Edward N. Walsh, New City, both of N.Y.

[73] Assignee: Stauffer Chemical Company, Westport, Conn.

[22] Filed: May 28, 1974

[21] Appl. No.: 473,468

[52] U.S. Cl. .......................... 260/928; 260/2.5 AJ; 260/2.5 AR; 260/978; 260/983
[51] Int. Cl.$^2$ .......................................... C07F 9/08
[58] Field of Search .................... 260/928, 978, 983

[56] References Cited
UNITED STATES PATENTS

| | | | |
|---|---|---|---|
| 3,641,202 | 2/1972 | Biranowski et al. | 260/928 X |
| 3,822,327 | 7/1974 | Weil | 260/928 |

*Primary Examiner*—Richard L. Raymond
*Attorney, Agent, or Firm*—Richard P. Fennelly

[57] ABSTRACT

Products which are phosphorus containing oligomers having

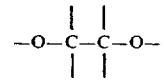

linkages between phosphorus atoms and which are obtained by the self-condensation of β-haloalkyl esters of pentavalent phosphorus acids or the condensation of these esters with alkyl esters of a pentavalent phosphorus acid are treated after residual acidity has been neutralized, e.g., with an alkylene oxide, with water and then with an alkylene oxide for a period of time which is sufficient to enable the water to open labile groups contained in the product and the alkylene oxide to neutralize any further acidity generated by the opening of such groups. The stabilized product formed by this process when incorporated to a polyurethane foam gives a foam having superior green strength to a polyurethane foam which is not treated in accordance with the invention.

7 Claims, No Drawings

METHOD OF PREPARING STABLE CONDENSATION PRODUCTS USING A WATER-ALKYLENE OXIDE TREATMENT AND PRODUCTS THEREFROM

TECHNICAL DESCRIPTION OF THE INVENTION

The present invention is a process for forming an improved condensation product of β-haloalkyl esters of pentavalent phosphorus acids which have flame retardant properties. A number of processes for formation of the class of compounds of interest herein are described in the patent literature and in copending applications including the following:

1. U.S. Patent No. 3,513,644 to Edward D. Weil which describes the preparation of polycondensed oligomeric phosphates by heating of tris(2-haloalkyl) phosphates.
2. U.S. Pat. Nos. 3,641,202 and 3,695,925 to Edward D. Weil which describe the preparation of oligomeric polycondensed phosphonates from bis (haloalkyl) vinyl phosphonates.
3. U.S. Pat. No. 3,896,187 of Edward D. Weil which describes liquid poly(haloethyl-ethyleneoxy) phosphoric acid esters prepared by condensing tris(2-haloethyl)phosphate.
4. U.S. Ser. No. 410,583, filed Nov. 12, 1973, now abandoned, and U.S. Pat. No. 3,855,359 of Edward D. Weil which describe the copolycondensation of certain phosphates and phosphonates having a 2-haloalkyl group on at least one of these reactants.
5. U.S. Pat. No. 3,822,327 of Edward D. Weil which describes homo- and co-polycondensates of bis(2-haloethyl) vinylphosphonates.
6. U.S. Pat. No. 3,891,727 of Edward D. Weil which relates generally to condensation products of haloalkyl esters of pentavalent phosphorus acids.

These patents and disclosures insofar as they relate to the condensation products usable in the practice of the instant invention are incorporated herein by reference.

The process of this invention is particularly applicable to the homocondensation product of tris(2-chloroethyl) phosphate, the copolycondensation product of bis(2-chloroethyl)vinylphosphonate and dimethyl methylphosphonate, to the copolycondensation product of bis(2-chloroethyl) vinylphosphonate and trimethyl phosphate, to the homopolycondensation product of bis (2-chloroethyl) vinylphosphonate, and to the copolycondensation product of tris(2-chloroethyl)-phosphate and dimethyl methylphosphonate.

Briefly, the polycondensation products are produced by reacting the monomers (both of which, as has already been noted, may be the same) to give off a volatile alkyl halide or alkylene dihalide and leave behind a non-volatile oligomeric condensation product.

The polycondensation reaction can be run without a catalyst, but, to permit lower temperatures and/or shorter reaction times, it is preferably conducted in the presence of a nucleophilic catalyst. Suitable quantities of catalyst are from a few parts per million, e.g., 50 p.p.m., up to about 10% by weight, preferably 0.01 – 5% based on weight of the reaction mixture.

The reaction mixture, with proper amount of catalyst, if desired, and in the desired molar ratio of starting materials, is heated to a temperature within the range of from about 110° to about 250°C., preferably 160°–180°C. Further details concerning the condensation reaction may be found in the disclosures previously incorporated herein by reference.

It has been suggested in U.S. Pat. No. 3,896,187 of Edward D. Weil, in Canadian Patent No. 908,186, and in Belgian Patent No. 789,815, that residual acidity in the type of product of interest herein could be removed by treatment with an alkylene oxide neutralizing agent until acidic groups in the product, i.e., the residual acid content, are present to an insignificant degree. Alternatively, it has been suggested in U.S. Pat. No. 3,891,727 of Edward D. Weil, that treatment with an alcohol or water and then with an epoxide be utilized. However, there was no suggestion in these prior art patents of using water and an alkylene oxide treatment after neutralization had been accomplished for an additional length of time to allow the water and alkylene oxide to act upon labile groups contained in the condensed product, e.g., pyro, cyclic, and bridged groups, and thereby neutralize any further acidity which would occur by the opening of said groups. This invention is particularly directed to continuing the treatment with water and an alkylene oxide until cyclic labile groups have been opened and neutralized.

The amount of water that should be added can range from about 0.3 to 10% by weight of the product that is treated and the water and condensed product is preferably aged at a temperature of about 50°–100°C for about 2–4 hours. This water treatment aids in opening cyclic bonds and other hydrolytically unstable bonds such as pyro and bridged structures, which are then neutralized by the subsequent alkylene oxide treatment. If desired the product can simply be washed with water until the cyclic bonds have been opened. It is well within the skill of a person in the art to devise how many water washes are needed. Generally one or four washes with 10%–80% by weight of water will suffice.

Any alkylene oxide can be used to treat the product after it has been treated with water. "Alkylene oxide" is therefore broadly intended to include any compound having an oxirane group

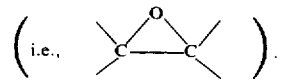

Illustrative of these compounds are ethylene oxide, propylene oxide, butylene oxide, styrene oxide, epichlorohydrin, epibromohydrin, diglycidyl ether, glycidyl butyl ether, glycidyl alkyl ether, glycidyl ether of phenol, diglycidyl ether of resorcinol, glycidyl ether of cresol and brominated cresol, glycidyl esters of acids such as acetic, acrylic and methacrylic acid, glycidol, diglycidyl ethers of bisphenol A and related epoxy resins made from bisphenol, or tetrahalobisphenols and epichlorohydrin, the diepoxide of dicyclopentylene ether, the diepoxide of vinylcyclohexene, the diepoxide of cyclohexenylmethyl cyclohexanecarboxylate, the diepoxide of bis(cyclohexenylmethyl) adipate, and the like. The alkylene oxide, that is added after residual acidity has been neutralized in the product and after the water treatment, is used in an amount sufficient to act upon the opened labile groups contained therein, e.g., generally from about 0.1% to about 10% by weight based on the total weight of the product. When a gaseous epixide, such as ethylene oxide, is employed, it may conveniently be passed in and through the reaction product until acidic groups have been treated. Treatment occurs after residual acidity alone has been removed, e.g., by treatment with an alkylene oxide such as described above for 3-8 hours at 90°-110°C. and after cyclic groups have opened in the water treatment. This will generally involve treating the product for about 1 hour to 10 hours, preferably from about 3-8 hours, after the treatment with water has been completed. Th unreacted excess which passes through can, if desired, be collected and recycled. The treatment with alkylene oxide is performed at a temperature of about 90°-140°C, preferably 90°-110°C.

The product formed by the process described herein when incorporated in a polyurethane foam formulation will produce a foam having superior green strength to the foam containing a condensed product not so treated. Poor green strength is demonstrated by a tacky top surface on the foam and/or a foam which tears easily after the initial cure.

The following working Examples illustrate the invention:

EXAMPLE 1

Five hundred grams of condensed tris(2-chloroethyl) phosphate was condensed in the presence of about 0.2% $Na_2CO_3$ at 165°C. The product was treated with ethylene oxide for about 3 hours until it was neutralized of residual acidity. This product was used for further testing as described.

EXAMPLE 2

The product (500g) from Example 1 was placed in a three neck 500 ml flask equipped with a distillation head, pot thermometer and magnetic stirrer. Distilled water (2.5g or 0.5%) was added and the mixture was heated to 60°C for 2 hours giving an acid number of 5.2mg KOH/g product in water-acetone after 20 min. Ethylene oxide was added at 100°C for 3½ hours. After 70g was used, the acid number was unmeasurable. The solution was aspirator stripped at 80°c/35mm for 25 min., and the acid number of the final product was 0.04mg KOH/g in water-acetone after 20 min.

EXAMPLE 3

Example 2 was repeated using 5.0g or 1.0% of water. After heating for 2 hours at 60°C the acid number was 6.0mg KOH/g (acetone-water; 20 min.). Treatment with about 50g of ethylene oxide for 3½ hours at 100°C reduced the acid number to near neutral. After aspirator stripping at 80°C/35mm for 25 minutes the acid number was 0.04mg KOH/g (acetone-water; 20 min.).

EXAMPLE 4

The product (12,000g) from Example 1, with the exception of the neutralization with ethylene oxide, was placed in a flask and heated to 100°C. Ethylene oxide (600g) was introduced for 8 hours and then was stripped. The acid number in water-acetone after 20 min. was 0.08 mg KOH/g. The mixture was heated to 60°C and 60g of water was added. The water and product were allowed to stand for 2 hours. Ethylene oxide (450) was again added at 100°C over a period of about 8 hours. The acid number in acetone-water after 20 min. was 0.04mg KOH/g.

EXAMPLE 5

The same product (12,000g) initially used in Example 5 was used again and 650g of ethylene oxide over an 8 hour period at 100°C was added. After stripping, the acid number was 0.05mg KOH/g. Sixty grams of water was added at 60°C and was allowed to remain for 2 hours. Then 240g (2% by weight) of ERL 4221 (the diepoxide of cyclohexenylmethyl cyclohexenecarboxylate) was added at 100°C for 3 hours. The heating was continued for an additional three hours. After stripping, the acid number was unmeasureable in water-acetone after 20 minutes.

EXAMPLE 7

The products formed in Examples 1–5 were incorporated in a polyurethane foam formulation at 10 parts by weight. The other ingredients were:

| REAGENT | PARTS BY WEIGHT |
|---|---|
| Niax 16-46 Polyol (Union Carbide) | 100 |
| $H_2O$ | 4.0 |
| Niax A-1 Catalyst | 0.1 |
| N-ethyl morpholine | 0.2 |
| L548 Silicone | 1.0 |
| T-10 Stannous Octoate (50% in dioctyl phthalate) | 0.4 |
| Toluene Diisocyanate (80% 2,4 isomer, 20%-2,6 isomer) | 51.0 |

The foam was cured for 10 minutes at 125°C and was examined for its physical properties. The Table below sets forth the green strength of the foam. Green strength is a measure of the proper gelation and easily handling characteristics. Poor green strength is demonstrated by a tacky top surface on the foam and/or foam structure which tears easily after the initial cure. Condensed products that are not treated in accordance with the present invention demonstrate such inferior physical properties.

| PRODUCT | GREEN STRENGTH |
|---|---|
| Example 1 | Poor |
| Example 2 | Good |
| Example 3 | Good |
| Example 4 | Excellent |
| Example 5 | Excellent |

The condensation products of β-haloalkyl esters of pentavalent phosphorus acids which are meant to be included herein are those formed by self-condensation of such esters or of condensation of such esters with other alkyl esters of pentavalent phosphorus acids. In addition to the particular condensation products described above, this definition also includes the type of condensation products described in U.S. Pat. No. 3,764,640 to Klose.

What is claimed:

1. A process for forming a stabilized condensation product, which is adapted to be incorporated in a polyurethane foam, derived from condensing a β-haloalkyl ester of a pentavalent phosphorus acid with itself or with an alkyl ester of a pentavalent phosphorus acid to form a condensation product which comprises treating said condensation product after residual acidity has been neutralized with from about 0.3% to 10%, by weight of said product, of water for about 2 to 4 hours at about 50° to 100°C and thereafter with about 0.1% to about 10%, by weight of said product, of an alkylene oxide for about 1 to about 10 hours at about 90°C. to 140°C. to open labile groups contained in the product and to neutralize those groups.

2. A process as claimed in claim 1 wherein the alkylene oxide is added at a temperature of about

90°–110°C.

3. A process as claimed in claim 1 wherein the alkylene oxide treatment is carried out for about 3–8 hours.

4. A process as claimed in claim 1 wherein the alkylene oxide which is added is ethylene oxide.

5. A process as claimed in claim 1 wherein the condensation product which is treated is selected from the group consisting of the homocondensation product of tris(2-chloroethyl) phosphate, the copolycondensation product of bis(2-chloroethyl) vinylphosphonate and dimethyl methylphosphonate, the copolycondensation product of bis(2-chloroethyl) vinylphosphonate and trimethyl phosphate, the homocondensation product of bis(2-chloroethyl) vinylphosphonate, and the copolycondensation product of tris(2-chloroethyl) phosphate and dimethyl methylphosphate.

6. The product formed from the process of claim 1.

7. A stabilized product formed by the process of claim 5.

* * * * *